United States Patent [19]

Momoda et al.

[11] Patent Number: 5,808,100
[45] Date of Patent: Sep. 15, 1998

[54] CHROMENE COMPOUNDS AND PHOTOCHROMIC MATERIALS

[75] Inventors: Junji Momoda; Tadashi Hara, both of Tokuyama, Japan

[73] Assignee: Tokuyama Corporation, Tokuyama, Japan

[21] Appl. No.: 759,704

[22] Filed: Dec. 6, 1996

[30] Foreign Application Priority Data

Dec. 6, 1995 [JP] Japan ................................. 7-317991

[51] Int. Cl.$^6$ ................................. C07D 409/01
[52] U.S. Cl. ........................... 549/60; 252/586; 359/885; 546/196; 548/203; 548/235; 548/525; 549/58; 549/389
[58] Field of Search ................ 549/60, 58, 389; 548/203, 235, 525; 546/196; 252/585; 359/885

[56] References Cited

U.S. PATENT DOCUMENTS 3,567,605  3/1971  Becker .
5,200,116  4/1993  Heller .
5,238,981  8/1993  Knowles .
5,543,533  8/1996  Allegrini ................................. 549/389

FOREIGN PATENT DOCUMENTS 0629620   12/1994  European Pat. Off. .
7/206858  8/1995   Japan ..................................... 549/60
WO9317071 9/1993   WIPO .
WO9500867 1/1995   WIPO .

OTHER PUBLICATIONS

Patent Abstracts of Japan, vol. 95, No. 11, 26 Dec. 1995 and JP 07 206858 A (Hodogaya Chem. Co.), 8 Aug. 1995.

*Primary Examiner*—Robert Gerstl
*Attorney, Agent, or Firm*—Sherman and Shalloway

[57] ABSTRACT

A photochromic compound which is initially colored less, exhibits excellent durability and features high color density and high color fading rate, and a photochromic material thereof. The photochromic compound basically has two aromatic heterocyclic groups or an aromatic heterocyclic group and a naphthyl group at the third position, and has a benzene ring that is condensed at the f-th position.

15 Claims, 1 Drawing Sheet

CHROMENE COMPOUNDS AND PHOTOCHROMIC MATERIALS

BACKGROUND OF THE INVENTION

1. Field of the Invention

The present invention relates to a novel chromene compound which changes into a form of being colored upon being irradiated with light containing ultraviolet rays such as sunlight or light from a mercury lamp, the change being reversible and the chromene compound exhibiting excellent durability.

2. Description of the Prior Art

Photochromism is a phenomenon which is drawing attention in recent several years, and is a reversible action in which the color quickly changes when a certain compound is irradiated with light containing ultraviolet rays such as sunlight or light from a mercury lamp, and the initial color is resumed when the compound is placed in a dark place without being irradiated with light. A compound having such a property is called photochromic compound. Compounds that exhibit various colors have heretofore been synthesized without, however, any common properties in their structures.

U.S. Pat. No. 3,567,605 discloses a chromene compound represented by the following formula (A),

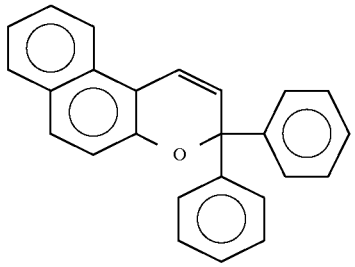

(A)

This chromene compound exhibits photochromic property nearly at room temperature (20° to 30° C.) but develops color of a low density when it is irradiated with ultraviolet rays and is not practicable.

WO9317071 discloses a chromene compound represented by the following formula (B),

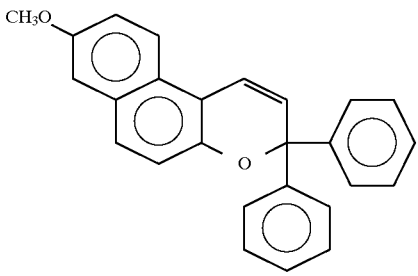

(B)

and WO9500867 discloses a chromene compound represented the following formula (C),

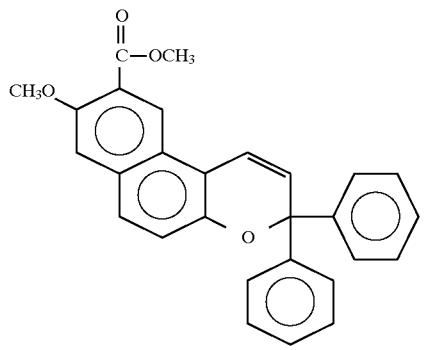

(C)

These two compounds develop colors at densities higher than the color density of the compound disclosed in the above-mentioned U.S. Pat. No. 3,567,605, but are not satisfactory in regard to their durability for photochromic properties. Besides, the color fading rate is so slow that they are not practically satisfactory.

EP629620 discloses a chromene compound represented by the following formula (D),

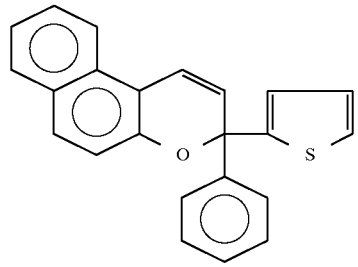

(D)

This chromene compound exhibits a large color fading rate but is not satisfactory in regard to the color density and is not practicable.

Japanese Laid-Open Patent Publication No. 206858/1995 discloses a chromene compound represented by the following formula (E),

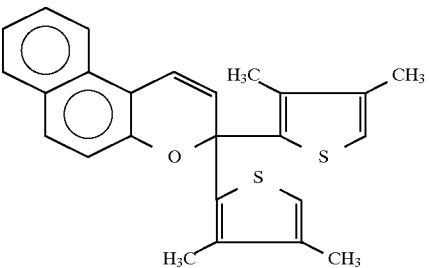

(E)

This chromene compound, however, has been initially colored to a remarkable degree and lacks transparency.

SUMMARY OF THE INVENTION

The object of the present invention therefore is to provide a chromene compound which exhibits further improved photochromic properties compared with those of the above-mentioned compounds, are initially colored less, exhibits a large color density, and has excellent durability.

The present invention was proposed in order to accomplish the above-mentioned object and was completed based upon the discovery by the present inventors in that a novel chromene compound is initially colored less and exhibits a high color density and excellent durability for photochromic properties.

That is, the present invention is concerned with a chromene compound represented by the following general formula (1),

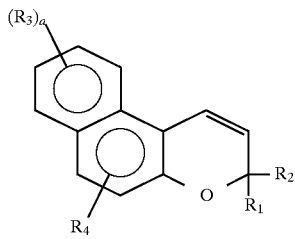
(1)

wherein $R_1$ is a group represented by the formula,

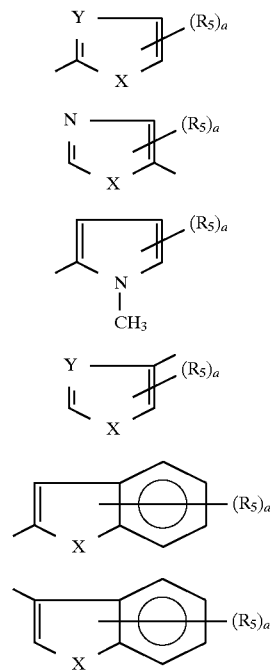

X is an oxygen atom or a sulfur atom, Y is a carbon atom or a nitrogen atom, $R_2$ is a group represented by the formula,

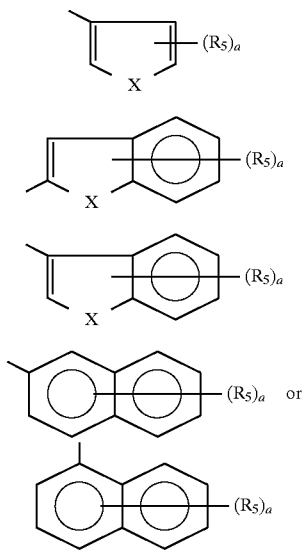

$R_3$, $R_4$ and $R_5$ may be the same or different and are each hydrogen atoms, alkyl groups, alkoxy groups, aralkyl groups, acyl groups, cyano groups, substituted amino groups, aryl groups, acyloxy groups, nitro groups, hydroxyl groups or halogen atoms, a denotes the number of the substituent $R_3$ or $R_5$ and is 1 or 2.

According to the present invention, furthermore, there is provided a photochromic material and, particularly, a photochromic lens containing a chromene compound represented by the above-mentioned general formula (1).

DETAILED DESCRIPTION OF THE PREFERRED EMBODIMENTS

Figure 1:
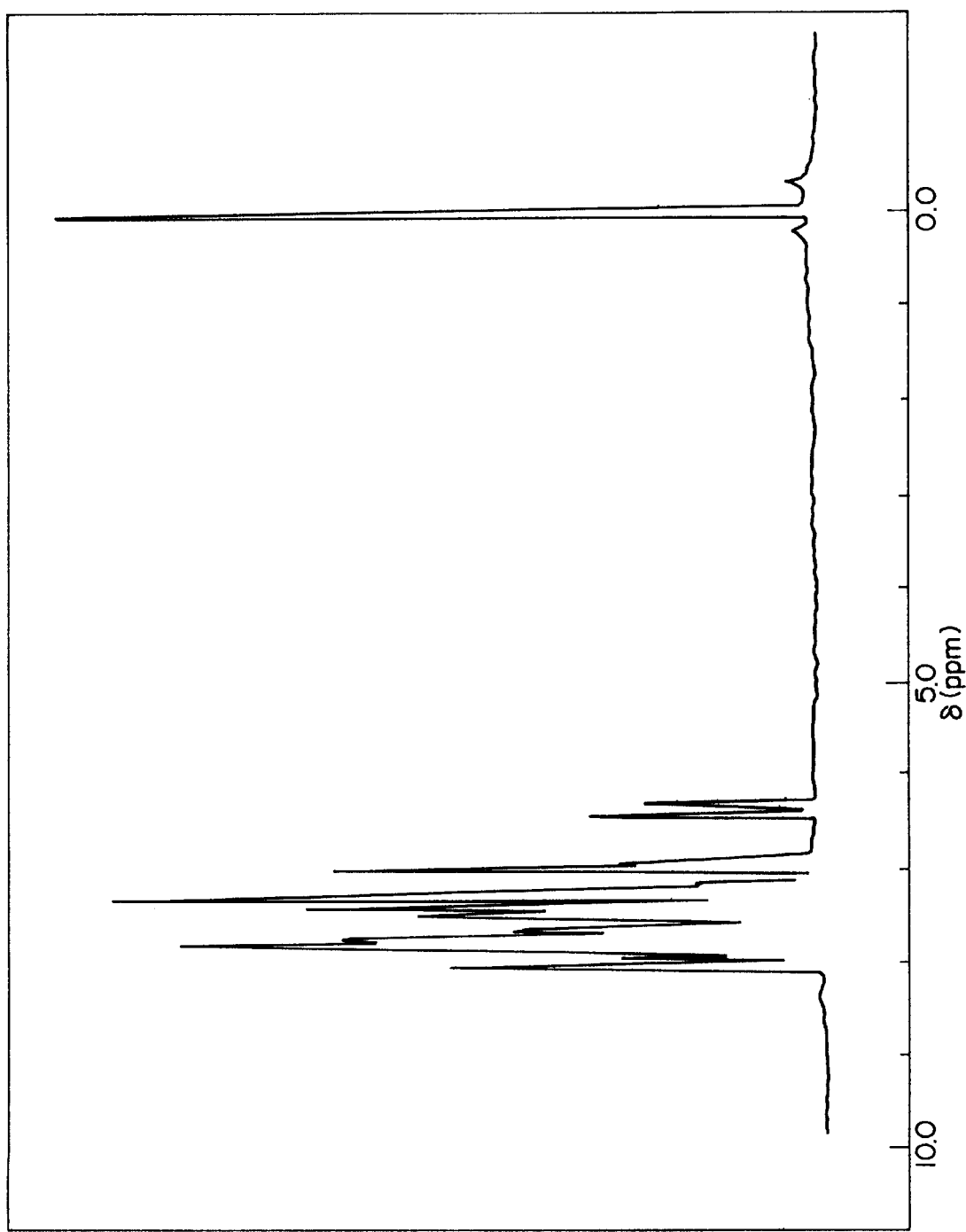
FIG. 1 is a diagram illustrating a proton nucleus magnetic resonance spectrum of a compound of Example 1.

In the chromene compound represented by the general formula (1), a group of the formula (i) which is the substituent R1 may be a substituted or unsubstituted 2-thienyl group, 2-furyl group, 2-oxazolyl group or 2-thiazolyl group, the group of the formula (ii) may be a substituted or unsubstituted 5-oxazolyl group or a 5-thiazolyl group, the group of the formula (iii) may be a substituted or unsubstituted 2-N-methylpyrrolyl group, the group of the formula (iv) may be a substituted or unsubstituted 3-thienyl group, 3-furyl group, 4-oxazolyl group, or 4-thiazolyl group, the group of the formula (v) may be a substituted or unsubstituted 2-benzothienyl group or 2-benzofuryl group, and the group of the formula (vi) may be a substituted or unsubstituted 3-benzothienyl group or 3-benzofuryl group.

The substituent R2 may be the group of the formula (vii) such as substituted or unsubstituted 3-thienyl group or 3-furyl group, group of the formula (viii) such as substituted or unsubstituted 2-naphthyl group, or group of the formula (ix) such as substituted or unsubstituted 1-naphthyl group, in addition to the groups of the formulas (v) and (vi).

In the chromene compound of the present invention, attention should be given to the fact that the group of the formula (i) such as 2-thienyl group or 2-furyl group may exist as one substituent R1 but is excluded from the other substituent R2. That is, the compound in which R1 and R2 are both 2-thienyl groups or 2-furyl groups is initially colored to a conspicuous degree and is not suited as a photochromic material. A chromene compound in which one substituent R1 is a 2-thienyl group or a 2-furyl group and the other substituent R2 is a group specified by the present invention, is excellent in regard to that it is not almost initially colored, exhibits a high color density and good durability.

A suitable substituent R1 may be the one in which Y is a carbon atom among the groups of the formulas (i) and (iv), or a group of the formula (v) or (vi). Among them, the group of the formula (i) or (iv) in which Y is a carbon atom is most preferred.

A suitable substituent R2 may be the one of the formula (viii) or (ix). Among them, the substituted or unsubstituted 1-naphthyl group is more desirable from the standpoint of exhibiting a larger color density than the 2-naphthyl group, but exhibits a low color fading rate.

As the alkyl groups, alkoxyl groups, aralkyl groups, acyl groups, substituted amino groups, aryl groups, acyloxy groups and halogen atoms represented by R3, R4 and R5 in the above-mentioned general formula (1), any widely known groups may be used without any limitation.

Though there is no particular limitation, the alkyl group may generally have 1 to 10 carbon atoms and, preferably, 1 to 4 carbon atoms. Concrete examples of the alkyl group include methyl group, ethyl group, n-propyl group, isopropyl group, n-butyl group, t-butyl group, etc.

Though there is no particular limitation, the alkoxy group may generally have 1 to 10 carbon atoms and, preferably, 1 to 4 carbon atoms. Concrete examples of the alkoxy group include methoxy group, ethoxy group, n-propoxy group, isopropoxy group, n-butoxy group, t-butoxy group, etc.

Though there is no particular limitation, the aralkyl group may generally have 7 to 16 atoms and, preferably, 7 to 10 carbon atoms. Concrete examples of the aralkyl group include benzyl group, phenylethyl group, phenylpropyl group, phenylbutyl group, etc.

Though there is no particular limitation, the acyl group may generally have 1 to 15 carbon atoms and, preferably, 1 to 7 carbon atoms. Concrete examples of the acyl group include formyl group, acetyl group, propionyl group, butyryl group, benzoyl group, etc.

Though there is no particular limitation, the substituted amino group may generally have a substituent such as an alkyl group with 1 to 10 carbon atoms or an alkyl group having hetero atoms. The substituents of these amino groups may form a ring. Concrete examples of the substituted amino group include methylamino group, ethylamino group, propylamino group, isopropylamino group, dimethylamino group, diethylamino group, methylethylamino group, 2-hydroxyethylamino group, di(2-hydroxyethyl)amino group, piperidino group, morpholino group, N-methylpiperadino group, thiomorpholino group, aziridino group and pyrrolidino group.

Though there is no particular limitation, the aryl group may generally have 6 to 20 carbon atoms and, preferably, 6 to 14 carbon atoms. Concrete examples of the aryl group include phenyl group, naphthyl group, tolyl group, etc.

Though there is no particular limitation, the acyloxy group may generally have 1 to 15 carbon atoms and, preferably, 2 to 7 carbon atoms. Concrete examples of the acyloxyl group include acetoxy group, propionyloxy group, benzoyloxy group, (meth)acryloyloxy group, etc.

Though there is no particular limitation, concrete examples of the halogen atom preferably used in the present invention may include fluorine, chlorine, bromine, etc.

In the general formula (1), "a" denotes the number of $R_3$ or $R_5$ and is 1 or 2. Though there is no particular limitation on the positions of the substituents $R_3$ and $R_4$, it is desired that $R_3$ is at the eighth or ninth position on the 3H-benzo(f) chromene skeleton of the general formula (1) and $R_4$ is at the sixth position.

There is no particular limitation on the position of the substituent $R_5$. However, an increased color density is obtained when the substituent $R_5$ is introduced to a carbon atom neighboring the position where the group of any one of the formulas (i) to (ix) is bonded, which is desirable.

Preferred chromene compounds of the present invention are exemplified below.

3-(2-Furyl)-3-(2-naphthyl)-3H-benzo(f) chromene;

3-(2-Furyl)-3-(3-furyl)-3H-benzo(f) chromene;

8-Methoxy-3-(2-thienyl)-3-(1-naphthyl)-3H-benzo(f) chromene;

3-(2-thienyl)-3-(1-fluoro-2-naphthyl)-3H-benzo(f) chromene;

3-(3-fluoro-2-thienyl)-3-(2-naphthyl)-3H-benzo(f) chromene;

3-(3-thienyl)-3-(1-naphthyl)-3H-benzo(f) chromene;

3-(2-furyl)-3-(3-thienyl)-3H-benzo(f) chromene; and 3-(2,5-dichloro-3-thienyl)-3-(2-naphthyl)-3H-benzo(f) chromene.

The compound represented by the above-mentioned general formula (1) of the present invention usually exists as a colorless or pale yellow solid or viscous liquid at normal temperature and under normal pressure, and can be confirmed by the following means (a) to (c).

(a) Upon measuring the proton nucleus magnetic resonance spectra ($^1$H-NMR), there appear peaks due to aromatic protons and protons of alkenes near δ6.0 to 9.0 ppm, and peaks due to protons of an alkyl group and an alkylene group near δ0.8 to 5.0 ppm. Upon comparing the spectral intensities, furthermore, the numbers of protons of the bonding groups can be learned.

(b) The composition of a corresponding product can be determined relying upon the elemental analysis.

(c) Upon measuring the $^{13}$C-nuclear magnetic resonance spectra ($^{13}$C-NMR), there appear peaks due to carbon of aromatic hydrocarbon groups near δ110 to 160 ppm, peaks due to carbon of alkenes near δ80 to 140 ppm, and peaks due to carbon of an alkyl group and an alkylene group near δ20 to 80 ppm.

The compound represented by the general formula (1) of the present invention can be obtained by any method without any particular limitation. Described below are representative methods that are generally favorably employed.

A method in which a compound represented by the following general formula (2),

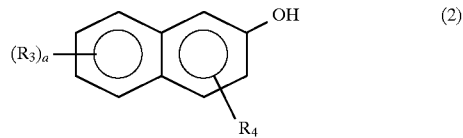

is reacted with a compound represented by the general formula (3),

in the presence of an acid catalyst. Here, $R_1$ to $R_4$ in the general formulas (2) and (3) have the same meanings as the substituents of the general formula (1).

The compound represented by the general formula (2) is reacted with the compound represented by the general formula (3) in a manner as described below. That is, the reaction ratio of these two compounds can be selected over a wide range but is, generally, selected over a range of from 1:10 to 10:1 (molar ratio). As the acid catalyst, there can be used sulfuric acid, benzenesulfonic acid, p-toluenesulfonic acid or the like in an amount over a range of from 0.1 to 10 parts by weight with respect to the sum of the reaction substrates represented by the above general formulas (2) and (3). The reaction temperature is usually from 0° to 200° C., and the solvent is a non-protonic organic solvent such as N-methylpyrrolidone, dimethylformamide, tetrahydrofurane, benzene, toluene, or the like.

The chromene compound represented by the above-mentioned general formula (1) of the present invention dissolves well in a general organic solvent such as toluene, chloroform or tetrahydrofurane. When the chromene compound represented by the general formula (1) is dissolved in such a solvent, the solution is usually colorless and is transparent, and exhibits a photochromic action in that the solution quickly develops a color when it is irradiated with sunlight or ultraviolet rays and quickly returns to the initial colorless state when the irradiation with light is shut off.

The photochromic action of the compound of the general formula (1) is also exhibited even in a high molecular solid matrix. Any high molecular solid matrix can be used provided it enables the chromene compound represented by the general formula (1) of the present invention to be homogeneously dispersed. Examples which are optically preferred include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethyl methacrylate), polydimethylsiloxane, polycarbonate, and the like.

There can be further exemplified thermosetting resins obtained by polymerizing radically polymerizable polyfunctional monomers such as polyhydric acrylic acid and polyhydric methacrylic acid ester compounds like ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl) propane, 2,2-bis(3,5-dibromo-4-methacryloyloxyethoxyphenyl) propane, etc.; polyhydric allyl compounds like diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate, trimethylolpropane triallyl carbonate, etc.; polyhydric thioacrylic acid and polyhydric thiomethacrylic acid ester compounds like 1,2-bis(methacryloylthio) ethane, bis(2-acryloylthioethyl) ether, 1,4-bis (methacryloylthiomethyl) benzene, etc.; acrylic acid ester compounds and methacrylic acid ester compounds like glycidyl acrylate, glycidyl methacrylate, β-methylglycidyl methacrylate, bisphenol A-monoglycidyl ether methacrylate, 4-glycidyloxymethacrylate, 3-(glycidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate, etc.; and divinyl benzene, etc.

Examples further include copolymers of these monomers and radically polymerizable monofunctional monomers such as unsaturated carboxylic acid like acrylic acid, methacrylic acid, maleic anhydride, etc.; acrylic acid and methacrylic acid ester compounds such as methyl acrylate, methyl methacrylate, benzyl methacrylate, phenyl methacrylate, 2-hydroxyethyl methacrylate, etc.; fumaric acid ester compounds such as diethyl fumarate, diphenyl fumarate, etc.; thioacrylic acid and thiomethacrylic acid ester compounds such as methylthioacrylate, benzylthioacrylate, benzylthiomethacrylate, etc.; and vinyl compounds such as styrene, chlorostyrene, methylstyrene, vinylnaphthalene, α-methylstyrene dimer, bromostyrene, etc.

There is no particular limitation in the method of dispersing the chromene compound represented by the general formula (1) of the present invention in the high molecular solid matrix, and a generally employed method can be used. For example, a method in which the thermoplastic resin and the chromene compound are melted and kneaded, and are dispersed in a resin, a method in which the chromene compound is dissolved in the above-mentioned polymerizable monomer, and is polymerized by heat or light while being added with a polymerization catalyst so as to be dispersed in the resin, or a method in which the chromene compound is dyed on the surface of the thermoplastic resin or the thermosetting resin and is dispersed in the resin.

The chromene compound of the present invention can be extensively used as a photochromic material, for example, as a memory material to substitute for silver salt photosensitive materials, or as a copying material, photosensitive material for printing, memory material for cathode-ray tubes, photosensitive material for laser, photosensitive material for holography, and the like memory material. Moreover, the photochromic material using the chromene compound of the present invention can be used as a material of photochromic lenses, as a material of optical filters, as a display material, as a material of actinometer and as an ornamental material. When the photochromic material is used, for example, for the photochromic lenses, any method may be employed without any particular limitation provided it is capable of offering a uniform dimming property. Concretely speaking, there can be employed a method in which a polymer film having a photochromic material of the present invention homogeneously dispersed therein is sandwiched between the lenses, a method in which the chromene compound of the present invention is dispersed in the above-mention ed polymerizable monomer and is polymerized according to a predetermined procedure, or a method in which the compound is dissolved in, for example, a silicone oil so as to infiltrate into the lens surfaces at 150° to 200° C. over a period of from 10 to 60 minutes, and the surfaces are coated with a curable material to obtain a photochromic lens. There can be further proposed a method in which the polymer film is applied onto the surfaces of the lens, and the surfaces are coated with a curable material to obtain a photochromic lens.

The chromene compound of the present invention is not initially colored in the solution or in the high molecular solid matrix, and exhibits excellent durability and a high color density. For instance, the photochromic lens using the chromene compound of the present invention is not deteriorated even after used for extended periods of time and exhibits excellent light-shielding property and permits the hue to change little. Moreover, since the chromene compound of the present invention exhibits a large color fading rate, a lens can be realized which does not interrupt the visual field when a person gets back to the indoors from the outdoors.

EXAMPLES

The present invention will be described in further detail by way of Examples to which only, however, the invention is in no way limited.

Example 1

1.44 Grams (0.01 mol) of a compound of the following formula

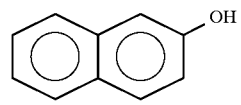

and 2.82 g (0.01 mol) of a compound of the following formula

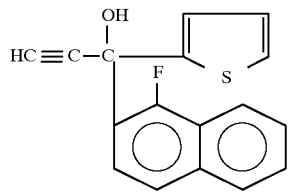

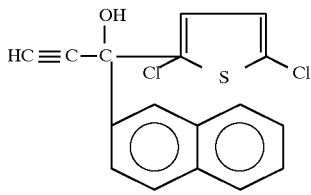

were dissolved in 70 ml of toluene followed by the addition of 0.05 g of p-toluenesulfonic acid, and were refluxed for 2 hours. After the reaction, the solvent was removed and was refined by chromatography on the silica gel to obtain 0.85 g of a pale yellowish powdery product.

Elemental analysis of the product showed C 79.35%, H 4.20%, O 3.97%, S 7.87% and F 4.69%, which were in very good agreement with C 79.35 %, H 4.17%, O 3.92%, S 7.84% and F 4.67% calculated from $C_{27}H_{17}O_1S_1F_1$.

Measurement of the proton nuclear magnetic resonance spectrum showed peaks of 17H due to aromatic protons and protons of alkenes near δ6.0 to 9.0 ppm as shown in FIG. 1.

Furthermore, measurement of a $^{13}$C-nuclear magnetic resonance spectrum showed a peak due to carbon of an aromatic ring near δ110 to 160 ppm and a peak due to carbon of an alkene near δ80 to 140 ppm.

It was confirmed from the above results that the product that was isolated was a compound represented by the following structural formula (5),

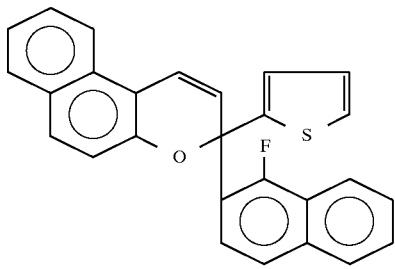

(5)

Example 2

1.44 Grams (0.01 mol) of a compound of the following formula

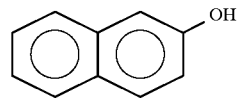

and 3.34 g (0.01 mol) of a compound of the following formula were dissolved in 50 ml of toluene followed by the addition of 0.05 g of sulfuric acid, and were refluxed for 2 hours. After the reaction, the solvent was removed and was refined by chromatography on the silica gel to obtain 1.19 g of a pale yellowish powdery product.

Elemental analysis of the product showed C 70.60%, H 3.50%, O 3.45%, S 6.99% and Cl 15.48%, which were in very good agreement with C 70.59%, H 3.48%, O 3.49%, S 6.97% and Cl 15.49% calculated from $C_{27}H_{16}O_1S_1Cl_2$.

Measurement of the proton nuclear magnetic resonance spectrum showed peaks of 16H due to aromatic protons and protons of alkenes near δ6.0 to 9.0 ppm.

Furthermore, measurement of a $^{13}$C-nuclear magnetic resonance spectrum showed a peak due to carbon of an aromatic ring near δ110 to 160 ppm and a peak due to carbon of an alkene near δ80 to 140 ppm.

It was confirmed from the above results that the product that was isolated was a compound represented by the following structural formula (6),

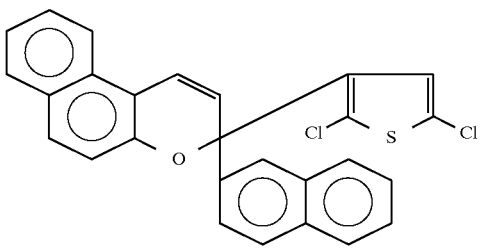

(6)

Examples 3 to 33

Chromene compounds shown in Table 1 were synthesized in the same manner as in Example 1. The obtained products were analyzed by using a similar means for confirming the structure as that of Example 1, and it was confirmed that they were the compounds represented by the structural formulas shown in Table 1. Table 2 shows elementally analyzed values of these compounds, values calculated from the structural formulas of the compounds and characteristic $^1$H-NMR spectra.

TABLE 1
| Example No. | Starting materials | Products | Yields (%) |
|---|---|---|---|
| 3 |  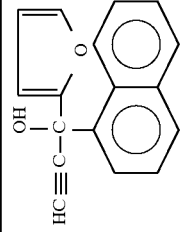 | 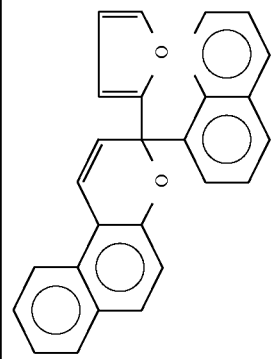 | 24 |
| 4 |  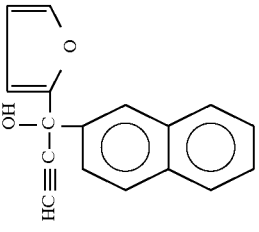 | 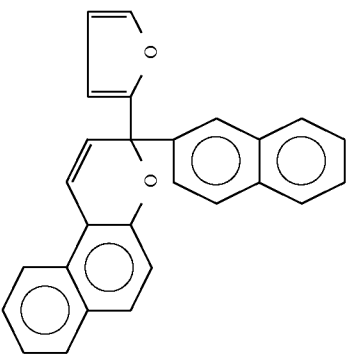 | 30 |
| 5 |  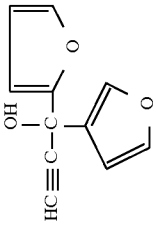 | 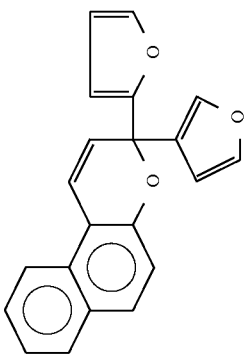 | 19 |

TABLE 1-continued

| Example No. | Starting materials | | Products | Yields (%) |
|---|---|---|---|---|
| 6 | (2-naphthol) | (propargyl alcohol with thiophene and furan substituents) | (chromene product with thiophene and furan substituents) | 28 |
| 7 | (2-naphthol) | (propargyl alcohol with fluorothiophene and naphthyl substituents) | (chromene product with fluorothiophene and naphthyl substituents) | 15 |
| 8 | (2-naphthol) | (propargyl alcohol with N-methylpyrrole and naphthyl substituents) | (chromene product with N-methylpyrrole and naphthyl substituents) | 8 |

TABLE 1-continued
| Example No. | Starting materials | Products | Yields (%) |
|---|---|---|---|
| 9 |  | 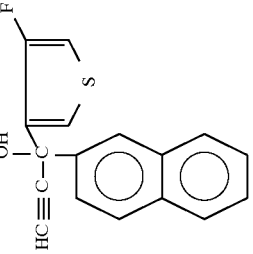 | 20 |
| 10 | 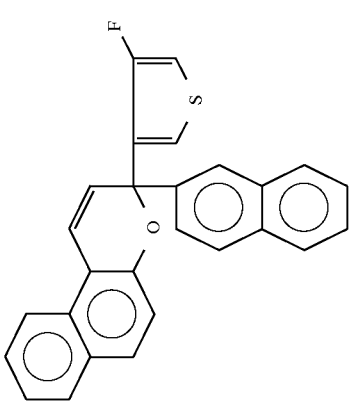 | 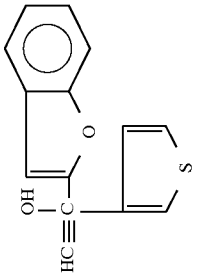 | 5 |
| 11 | 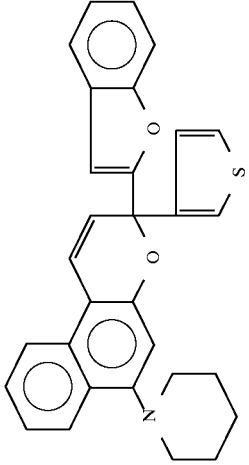 | 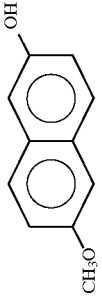 | 16 |

TABLE 1-continued

| Example No. | Starting materials | | Products | Yields (%) |
|---|---|---|---|---|
| 12 | (6-methoxy-3-acetyl-2-naphthol) | (propargyl alcohol with furan and 1-ethoxy-2-naphthyl) | (chromene product) | 22 |
| 13 | (6-benzyl-2-naphthol) | (propargyl alcohol with furan and 2-phenylthiophenyl) | (chromene product) | 6 |
| 14 | (6-methoxy-2-naphthol) | (propargyl alcohol with furan and benzofuranyl) | (chromene product) | 10 |

TABLE 1-continued

| Example No. | Starting materials | Products | Yields (%) |
|---|---|---|---|
| 15 | | | 17 |
| 16 | | | 4 |
| 17 | | | 39 |

TABLE 1-continued
| Example No. | Starting materials | Products | Yields (%) |
|---|---|---|---|
| 18 | 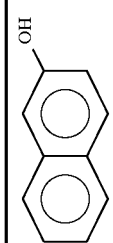 | 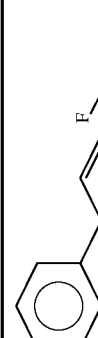 | 40 |
| 19 | 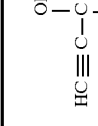 | 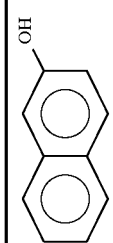 | 13 |
| 20 | 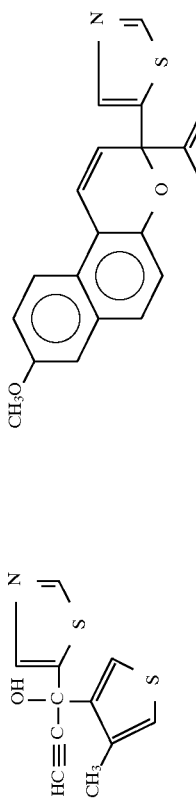 | 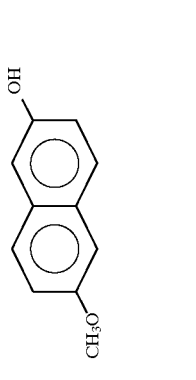 | 18 |

TABLE 1-continued
| Example No. | Starting materials | Products | Yields (%) |
|---|---|---|---|
| 21 | 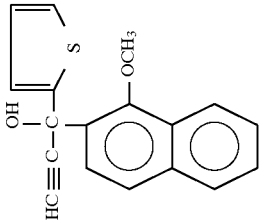 | 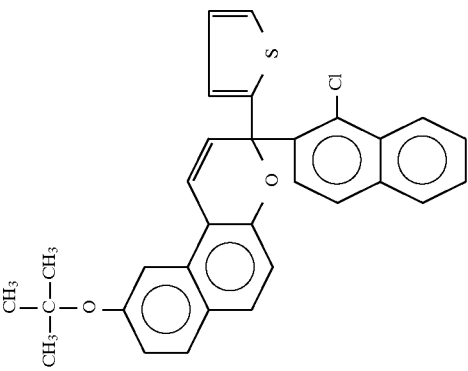 | 6 |
| 22 | 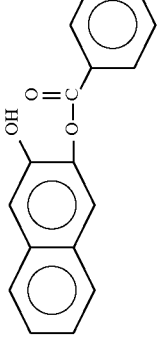 | 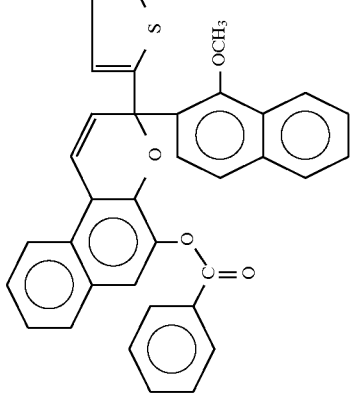 | 12 |

TABLE 1-continued
| Example No. | Starting materials | Products | Yields (%) |
|---|---|---|---|
| 23 | 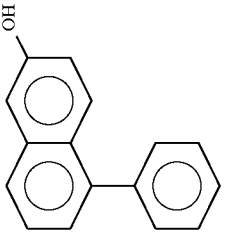 | 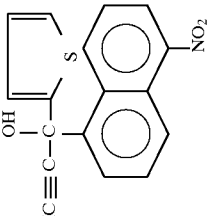 | 18 |
| 24 | 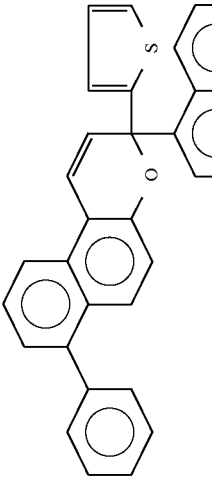 | 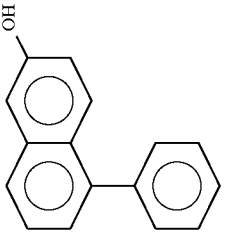 | 11 |
| 25 | 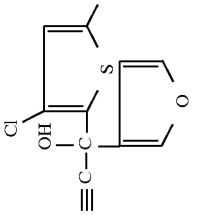 | 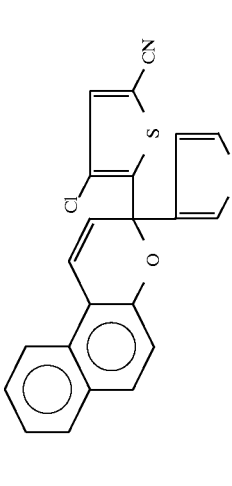 | 31 |

TABLE 1-continued
| Example No. | Starting materials | Products | Yields (%) |
|---|---|---|---|
| 26 | 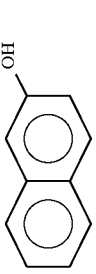 | 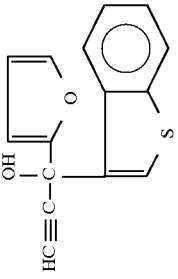 | 38 |
| 27 | 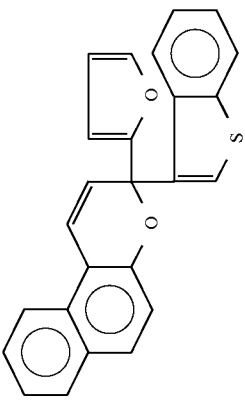 | 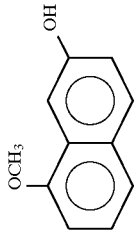 | 7 |
| 28 | 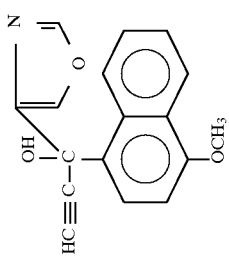 | 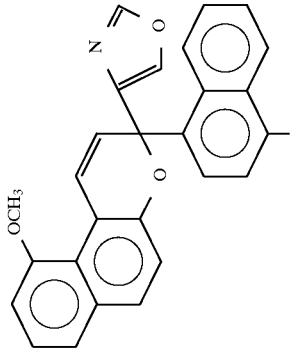 | 4 |

TABLE 1-continued

| Example No. | Starting materials | Products | Yields (%) |
|---|---|---|---|
| 29 | (3-methoxy-naphthalen-1-ol and acetylenic carbinol with phenylthio and 4-chloronaphthalen-2-yl) | (corresponding 2H-naphtho[1,2-b]pyran product) | 34 |
| 30 | (naphthalen-2-ol and acetylenic carbinol with 2-thienyl and 1-fluoronaphthalen-2-yl) | (corresponding 2H-naphtho[2,1-b]pyran product) | 28 |

TABLE 1-continued
| Example No. | Starting materials | Products | Yields (%) |
|---|---|---|---|
| 31 |  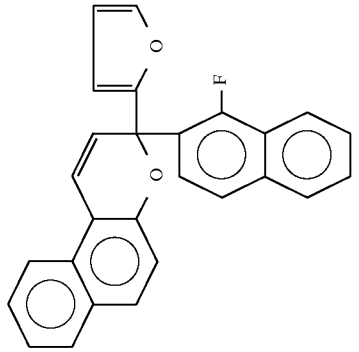 | 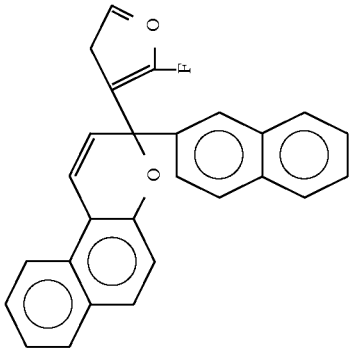 | 21 |
| 32 | 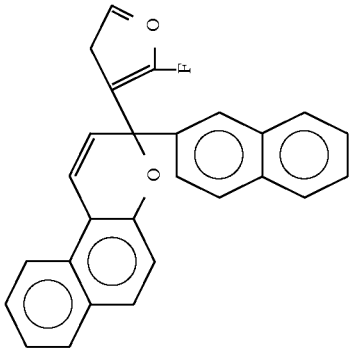 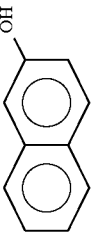 | 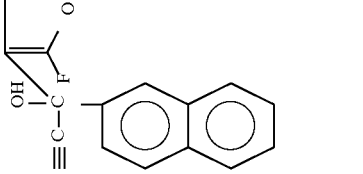 | 25 |

TABLE 1-continued
| Example No. | Starting materials | Products | Yields (%) |
|---|---|---|---|
| 33 |  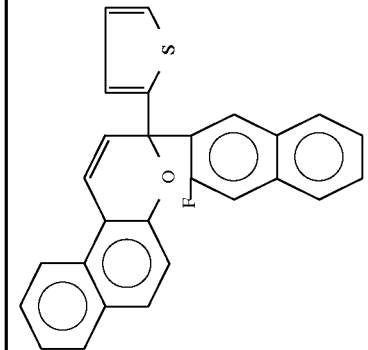 | 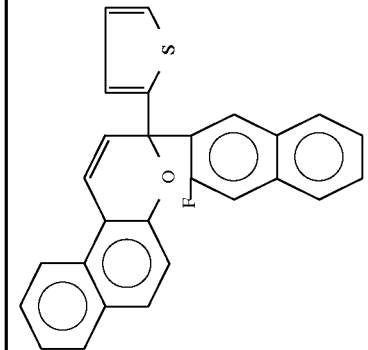 | 30 |

TABLE 2

| Example No. | Found | | | | | (%) Calculated | | | | | 1H-NMR spectra (ppm) δ |
|---|---|---|---|---|---|---|---|---|---|---|---|
| | C | H | N | O | others | C | H | N | O | others | |
| 3 | 86.65 | 4.85 | | 8.50 | | 86.63 | 4.81 | | 8.56 | | 6.9~9.0: 18 H |
| 4 | 86.60 | 4.77 | | 8.63 | | 86.63 | 4.81 | | 8.56 | | 6.9~9.0: 18 H |
| 5 | 80.25 | 4.50 | | 15.25 | | 80.25 | 4.46 | | 15.29 | | 6.9~9.0: 14 H |
| 6 | 76.40 | 4.33 | | 9.85 | S: 9.42 | 76.36 | 4.24 | | 9.70 | S: 9.70 | 6.9~9.0: 14 H |
| 7 | 79.33 | 4.21 | | 3.93 | S: 7.82<br>F: 4.71 | 79.41 | 4.34 | | 3.92 | S: 7.84<br>F: 4.66 | 6.9~9.0: 17 H |
| 8 | 86.78 | 5.45 | 3.64 | 4.11 | | 86.82 | 5.43 | 3.62 | 4.13 | | 6.9~9.0: 18 H<br>2.0~3.0: 3 H |
| 9 | 79.35 | 4.21 | | 3.92 | S: 7.85<br>F: 4.67 | 79.41 | 4.34 | | 3.92 | S: 7.84<br>F: 4.66 | 6.9~9.0: 17 H |
| 10 | 77.60 | 5.64 | 2.98 | 6.95 | S: 6.85 | 77.59 | 5.60 | 3.01 | 6.90 | S: 6.90 | 6.9~9.0: 16 H<br>1.0~3.5: 10 H |
| 11 | 80.06 | 4.62 | 3.48 | 11.84 | | 80.03 | 4.69 | 3.46 | 11.85 | | 6.9~9.0: 16 H<br>3.5~4.0: 3 H |
| 12 | 77.80 | 5.44 | | 16.76 | | 77.82 | 5.44 | | 16.74 | | 6.9~9.0: 15 H<br>1.0~4.5: 10 H |
| 13 | 78.99 | 4.45 | 3.00 | 6.78 | S: 6.78 | 78.98 | 4.46 | 2.98 | 6.79 | S: 6.79 | 6.9~9.0: 19 H<br>3.5~4.5: 2 H |
| 14 | 79.25 | 4.54 | | 16.21 | | 79.19 | 4.57 | | 16.24 | | 6.9~9.0: 15 H<br>3.5~4.5: 3 H |
| 15 | 80.62 | 4.61 | | 14.77 | | 80.56 | 4.63 | | 14.81 | | 6.9~9.0: 17 H<br>1.5~2.5: 3 H |
| 16 | 79.77 | 4.40 | 3.59 | 4.08 | S: 8.16 | 79.79 | 4.35 | 3.58 | 4.09 | S: 8.18 | 6.9~9.0: 17 H |
| 17 | 80.01 | 4.82 | | 7.69 | S: 7.68 | 80.08 | 4.76 | | 7.62 | S: 7.62 | 6.9~9.0: 17 H<br>3.8~4.0: 3 H |
| 18 | 79.50 | 4.22 | | 3.96 | S: 7.85<br>F: 4.65 | 79.41 | 4.17 | | 3.92 | S: 7.84<br>F: 4.66 | 6.9~9.0: 17 H |
| 19 | 67.55 | 4.34 | 3.60 | 8.16 | S: 16.35 | 67.52 | 4.35 | 3.58 | 8.18 | S: 16.37 | 6.9~9.0: 11 H<br>3.8~4.0: 6 H |
| 20 | 77.93 | 4.80 | | 10.32 | S: 6.95 | 77.92 | 4.76 | | 10.39 | S: 6.93 | 6.9~9.0: 16 H<br>1.5~2.5: 6 H |
| 21 | 74.88 | 5.04 | | 6.49 | S: 6.51<br>Cl: 7.09 | 74.92 | 5.04 | | 6.45 | S: 6.45<br>Cl: 7.09 | 6.9~9.0: 16 H<br>1.0~1.5: 9 H |
| 22 | 80.10 | 4.60 | | 9.91 | S: 6.11 | 80.15 | 4.58 | | 9.16 | S: 6.11 | 6.9~9.0: 21 H<br>3.8~4.0: 3 H |
| 23 | 77.43 | 4.12 | 2.75 | 9.39 | S: 6.31 | 77.50 | 4.11 | 2.74 | 9.39 | S: 6.26 | 6.9~9.0: 21 H |
| 24 | 67.85 | 3.10 | 3.50 | 8.24 | S: 8.22<br>Cl: 9.09 | 67.78 | 3.08 | 3.59 | 8.22 | S: 8.22<br>Cl: 9.11 | 6.9~9.0: 12 H |
| 25 | 82.45 | 4.36 | | 13.19 | | 82.42 | 4.39 | | 13.19 | | 6.9~9.0: 16 H |
| 26 | 78.99 | 4.22 | | 8.41 | S: 8.36 | 78.95 | 4.21 | | 8.42 | S: 8.42 | 6.9~9.0: 16 H |
| 27 | 77.20 | 4.80 | 3.27 | 14.73 | | 77.24 | 4.83 | 3.22 | 14.71 | | 6.9~9.0: 15 H<br>3.5~4.0: 6 H |
| 28 | 78.47 | 5.49 | 5.94 | 3.33 | S: 6.77 | 78.48 | 5.48 | 5.91 | 3.37 | S: 6.76 | 6.9~9.0: 16 H<br>1.5~4.0: 10 H |
| 29 | 76.45 | 4.15 | | 6.36 | S: 6.37<br>Cl: 7.07 | 76.11 | 4.16 | | 6.34 | S: 6.34<br>Cl: 7.05 | 6.9~9.0: 18 H<br>3.8~4.0: 3 H |
| 30 | 79.32 | 4.20 | | 3.93 | S: 7.86<br>F: 4.69 | 79.41 | 4.17 | | 3.92 | S: 7.84<br>F: 4.66 | 6.9~9.0: 17 H |
| 31 | 82.66 | 4.35 | | 8.14 | F: 4.85 | 82.65 | 4.34 | | 8.16 | F: 4.85 | 6.9~9.0: 17 H |
| 32 | 82.63 | 4.32 | | 8.16 | F: 4.85 | 82.65 | 4.34 | | 8.16 | F: 4.85 | 6.9~9.0: 17 H |
| 33 | 79.33 | 4.21 | | 3.92 | S: 7.84<br>F: 4.70 | 79.41 | 4.17 | | 3.92 | S: 7.84<br>F: 4.66 | 6.9~9.0: 17 H |

Examples 34 to 66, Comparative Examples 1 to 4

0.05 Parts of the chromene compound obtained in Example 1 was added to 70 parts of a tetraethylene glycol dimethacrylate, 15 parts of a triethylene glycol dimethacrylate, 10 parts of a glycidyl methacrylate and 5 parts of a 2-hydroethyl methacrylate, and was mixed to a sufficient degree. The mixture solution was poured into a mold constituted by a glass plate and a gasket made from an ethylene/vinyl acetate copolymer and then polymerized. The polymerization was conducted by using an air furnace while gradually raising the temperature up to 30° C. to 90° C. over a period of 18 hours, the temperature being maintained at 90° C. for two hours. After the polymerization, the polymer was taken out from the glass mold.

The obtained polymer (2 mm thick) was irradiated with light from a xenon lamp L-2480 (300 W) SHL-100 manufactured by Hamamatsu Photonics Co. through an Aero Mass filter (manufactured by Corning Co.) for 120 seconds under the conditions of 20° C.±1° C., beam intensities of 365 nm=2.4 mW/cm$^2$ and 245 nm=24 $\mu$W/cm$^2$ on the polymer surface to develop color and to measure photochromic properties. The photochromic properties were expressed as described below. The results were as shown in Table 3.

Maximum absorption wavelength ($\lambda$max): $\lambda$max of the polymer after it has developed color was found by using a spectrophotometer (instantaneous multi-channel photodetector MCPD1000) manufactured by Otsuka Denshi Kogyo Co.

ε(120): Absorbancy of the polymer using light of a maximum absorption wavelength after it was irradiated under the above-mentioned conditions for 120 seconds.

ε(0): Absorbancy of the polymer that has not been irradiated using light of a wavelength same as the maximum absorption wavelength of light with which the polymer was irradiated.

ε(120)−ε(0): Color density

Color fading rate [$t_{1/2}$]: Time required by the polymer irradiated for 120 seconds until the absorbancy decreases down to one-half of [ε(120)−ε(0)]. Durability [$T_{1/2}$]: Time required until the absorbency at the maximum absorption wavelength decreases down to ½ of the initial absorbency as measured by using a xenon fadometer FAC-25AX-HC manufactured by Suga Shikenki Co.

The photochromic polymers were obtained in the same manner as described above but using the compounds obtained in Examples 2 to 33 as chromene compounds. Properties were as shown in Table 3. For the purpose of comparison, properties of the compounds represented by the following formulas (A), (B), (D) and (E) were also shown in Table 3.

(A)

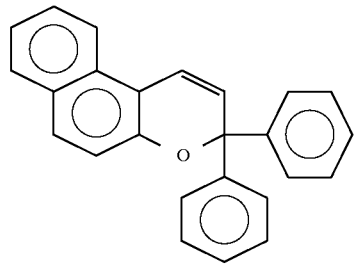

-continued (B)

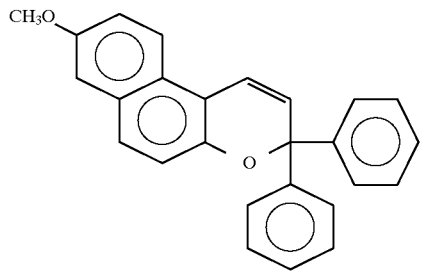

(D)

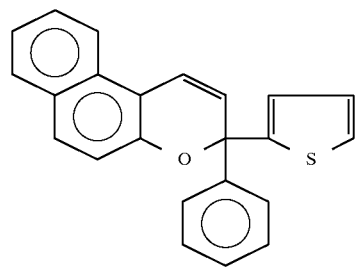

(E)

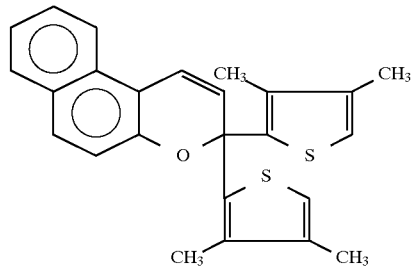

TABLE 3

| Example No. | Compound No. | $T_{1/2}$ (hour) | Developed Color tone λMax (nm) | ε (120) − ε (0) | ε (0) | $t_{1/2}$ (sec) |
| --- | --- | --- | --- | --- | --- | --- |
| 34 | 1 | 510 | 456 | 1.50 | 0.04 | 72 |
| 35 | 2 | 480 | 460 | 1.06 | 0.05 | 75 |
| 36 | 3 | 480 | 496 | 1.49 | 0.08 | 83 |
| 37 | 4 | 490 | 486 | 1.10 | 0.07 | 59 |
| 38 | 5 | 540 | 466 | 1.11 | 0.07 | 50 |
| 39 | 6 | 520 | 464 | 1.02 | 0.07 | 45 |
| 40 | 7 | 500 | 456 | 1.30 | 0.05 | 62 |
| 41 | 8 | 440 | 486 | 1.00 | 0.06 | 60 |
| 42 | 9 | 500 | 452 | 1.08 | 0.04 | 56 |
| 43 | 10 | 510 | 460 | 1.33 | 0.10 | 82 |
| 44 | 11 | 490 | 476 | 1.36 | 0.05 | 74 |

TABLE 3-continued

| Example No. | Compound No. | $T_{1/2}$ (hour) | Developed Color tone λMax (nm) | $\epsilon(120) - \epsilon(0)$ | $\epsilon(0)$ | $t_{1/2}$ (sec) |
|---|---|---|---|---|---|---|
| 45 | 12 | 450 | 510 | 1.34 | 0.08 | 66 |
| 46 | 13 | 490 | 480 | 1.02 | 0.07 | 62 |
| 47 | 14 | 480 | 484 | 1.06 | 0.07 | 60 |
| 48 | 15 | 480 | 462 | 1.23 | 0.05 | 81 |
| 49 | 16 | 485 | 466 | 1.09 | 0.06 | 42 |
| 50 | 17 | 470 | 502 | 1.23 | 0.05 | 84 |
| 51 | 18 | 505 | 456 | 1.15 | 0.04 | 68 |
| 52 | 19 | 450 | 490 | 1.46 | 0.06 | 75 |
| 53 | 20 | 480 | 506 | 1.42 | 0.05 | 89 |
| 54 | 21 | 470 | 450 | 1.35 | 0.05 | 70 |
| 55 | 22 | 450 | 486 | 1.51 | 0.06 | 85 |
| 56 | 23 | 430 | 472 | 1.15 | 0.08 | 68 |
| 57 | 24 | 480 | 458 | 1.12 | 0.05 | 65 |
| 58 | 25 | 540 | 492 | 1.23 | 0.06 | 59 |
| 59 | 26 | 510 | 460 | 1.05 | 0.06 | 50 |
| 60 | 27 | 490 | 480 | 1.50 | 0.08 | 89 |
| 61 | 28 | 450 | 458 | 1.01 | 0.05 | 60 |
| 62 | 29 | 480 | 440 | 1.30 | 0.12 | 82 |
| 63 | 30 | 495 | 450 | 1.18 | 0.04 | 70 |
| 64 | 31 | 490 | 480 | 1.44 | 0.06 | 80 |
| 65 | 32 | 490 | 450 | 1.28 | 0.05 | 65 |
| 66 | 33 | 495 | 460 | 1.11 | 0.04 | 68 |
| Comp. Ex. 1 | A | 460 | 436 | 0.52 | 0.04 | 40 |
| Comp. Ex. 2 | B | 240 | 472 | 0.74 | 0.04 | 90 |
| Comp. Ex. 3 | D | 490 | 466 | 0.51 | 0.04 | 42 |
| Comp. Ex. 4 | E | 485 | 514 | 0.86 | 0.26 | 75 |

Compared to the compounds of Comparative Examples 1 and 3, the compounds of the present invention develop color which is about twice as dense and exhibit excellent durability. Compared to the compound of Comparative Example 2, furthermore, the compounds of the present invention exhibit durability which is about twice as high and further exhibit excellent color fading rates. Compared to the compound of Comparative Example 4, the compounds of the present invention exhibit initial color which is smaller than one-half and further exhibit excellent light transmission factors.

We claim:

1. A chromene compound represented by the following general formula (1),

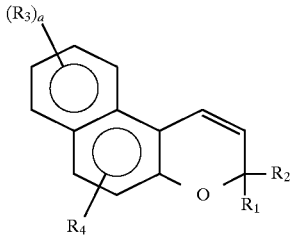

(1)

wherein $R_1$ is a group represented by the formula,

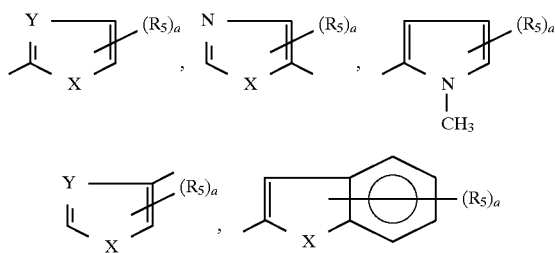

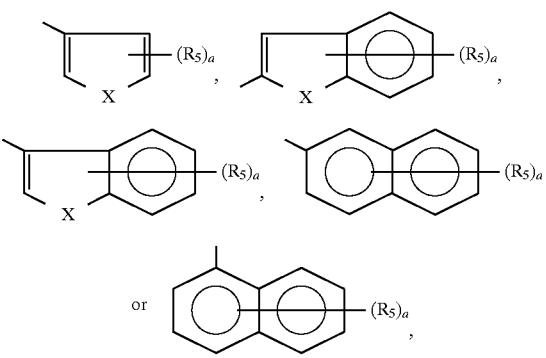

X is an oxygen atom or a sulfur atom, Y is a nitrogen atom, $R_2$ is a group represented by the formula, and $R_3$, $R_4$ and $R_5$ may be the same or different and are each hydrogen atoms, $C_1$ to $C_4$ alkyl groups, $C_1$ to $C_4$ alkoxy groups, $C_7$ to $C_{10}$ aralkyl groups, $C_1$ to $C_7$ acyl groups, cyano groups, $C_1$ to $C_{10}$ substituted amino groups, $C_6$ to $C_{14}$ aryl groups, $C_2$ to $C_7$ acyloxy groups, nitro groups, hydroxyl groups or halogen atoms, "a" denotes the number of the substituent $R_3$ or $R_5$ and is 1 or 2.

2. A chromene compound represented by the following general formula,

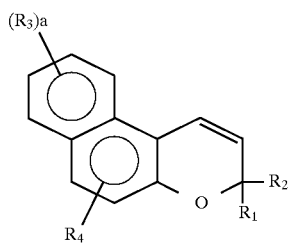

wherein $R_1$ is a group represented by the formula,

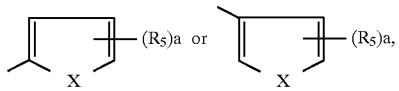

X is an oxygen or a sulfur atom, $R_2$ is a group represented by the formula,

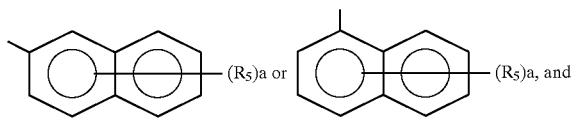

$R_3$, $R_4$ and $R_5$ may be the same or different and are each hydrogen atoms, $C_1$ to $C_7$ alkyl groups, $C_1$ to $C_4$ alkoxy groups, $C_7$ to $C_{10}$ aralkyl groups, $C_1$ to $C_7$ acyl groups, cyano groups, $C_1$ to $C_{10}$ substituted amino groups, C6 to $C_{14}$ aryl groups, $C_2$ to $C_7$ acyloxy groups, nitro groups, hydroxyl groups or halogen atoms, "a" denotes the number of the substituent $R_3$ or $R_5$ and is 1 or 2.

3. A chromene compound represented by the following general formula (1),

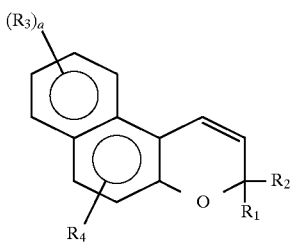  (1)

wherein $R_1$ is a group represented by the formula,

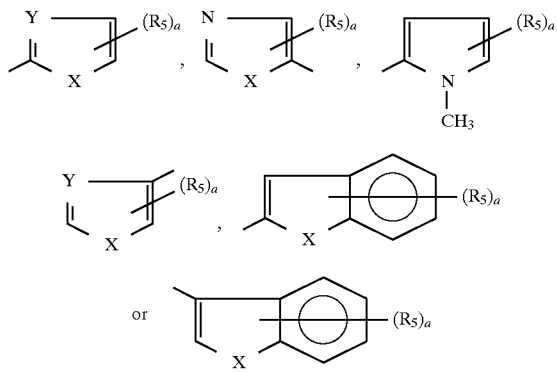

X is an oxygen atom or a sulfur atom, Y is a carbon atom, $R_2$ is a group represented by the formula,

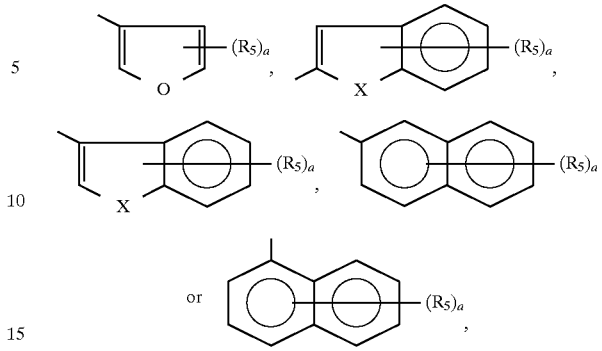

and
$R_3$, $R_4$ and $R_5$ may be the same or different and are each hydrogen atoms, $C_1$ to $C_4$ alkyl groups, $C_1$ to $C_4$ alkoxy groups, $C_7$ to $C_{10}$ aralkyl groups, $C_1$ to $C_7$ acyl groups, cyano groups, $C_1$ to $C_{10}$ substituted amino groups $C_6$ to $C_{14}$ aryl groups, $C_2$ to $C_7$ acyloxy groups, nitro groups, hydroxyl groups or halogen atoms, "a" denotes the number of the substituent $R_3$ or $R_5$ and is 1 or 2.

4. A chromene compound according to claim 3, wherein the chromene compound is represented by the following general formula,

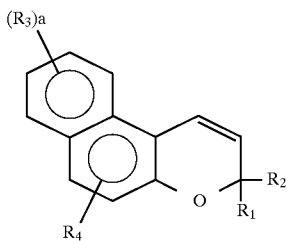

wherein $R_1$ is a group represented by the formula,

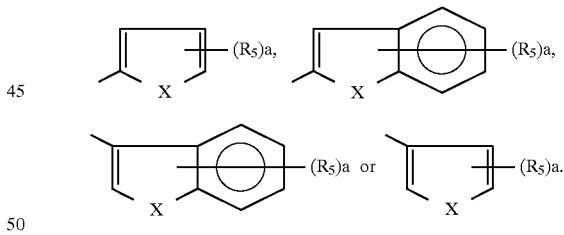

5. A chromene compound according to claim 2, wherein the chromene compound is a 3-(2-furyl)-3-(2-naphthyl)-3H-benzo(f) chromene.

6. A chromene compound according to claim 3, wherein the chromene compound is a 3-(2-furyl)-3-(3-furyl)-3H-benzo(f) chromene.

7. A chromene compound according to claim 2, wherein the chromene compound is an 8-methoxy-3-(2-thienyl)-3-(1-naphthyl)-3H-benzo(f) chromene.

8. A chromene compound according to claim 2, wherein the chromene compound is a 3-(2-thienyl)-3-(1-fluoro-2-naphthyl)-3H-benzo(f) chromene.

9. A chromene compound according to claim 2, wherein the chromene compound is a 3-(3-fluoro-2-thienyl)-3-(2-naphthyl)-3H-benzo(f) chromene.

10. A chromene compound according to claim 2, wherein the chromene compound is a 3-(3-thienyl)-3-(1-naphthyl)-3H-benzo(f) chromene.

11. A chromene compound wherein the chromene compound is a 3-(2-furyl)-3-(3-thienyl)-3H-benzo(f) chromene.

12. A chromene compound according to claim 2, wherein the chromene compound is a 3-(2,5-dichloro-3-thienyl)-3-(2-naphthyl)-3H-benzo(f) chromene.

13. A photochromic material comprising a chromene compound according to claim 1, 2 or 3 dissolved in a solvent or dispersed in a solid material.

14. A photochromic lens containing a chromene compound according to claim 1, 2 or 3 dispersed in a solid matrix lens material.

15. A chromene compound according to claim 1, 2 or 3, wherein $R_3$ to $R_5$ are the same or different and are members selected from the group consisting of hydrogen atom, methyl group, methoxy group, ethoxy group, t-butoxy group, benzyl group, acetyl group, acetate group, benzoyloxy group, phenyl group, piperizino group, nitro group, chlorine atom, flourine atom and cyano group.

* * * * *